(12) United States Patent
Teal et al.

(10) Patent No.: US 8,088,366 B2
(45) Date of Patent: ***Jan. 3, 2012

(54) ATTRACTANT FOR INDIAN MEAL MOTH LARVE

(75) Inventors: Peter E. A. Teal, Gainesville, FL (US); Don L. Silhacek, Gainesville, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 177 days.

This patent is subject to a terminal disclaimer.

(21) Appl. No.: 12/365,345

(22) Filed: Feb. 4, 2009

(65) Prior Publication Data

US 2010/0196307 A1      Aug. 5, 2010

(51) Int. Cl.
*A01N 43/08* (2006.01)
*A01P 19/00* (2006.01)

(52) U.S. Cl. .......................................... 424/84; 514/461

(58) Field of Classification Search ........................ None
See application file for complete search history.

(56) References Cited

U.S. PATENT DOCUMENTS 4,433,002 A * 2/1984 Zilch .............................. 426/640

OTHER PUBLICATIONS

Buttery et al. "Raisin and Dried Fig Volatile Components: Possible Insect Attractants" in:Teranishi et al., Qualtiy of Selected Fruits and Vegetables of North America (1981). pp. 29-41.*
Napasol, The Indian meal moth *Plodia interpunctella* (2007).*

* cited by examiner

*Primary Examiner* — Johann Richter
*Assistant Examiner* — Frank Choi
(74) *Attorney, Agent, or Firm* — John D. Fado; Robert D. Jones (57) ABSTRACT

A composition containing 2-pentylfuran is an effective attractant for the larvae of the Indian meal moth (*Plodia interpunctella*). The composition may be used alone or with a carrier component. The composition may be used in combination with any insect trapping means known in the art, as required for a specific application.

5 Claims, 15 Drawing Sheets

ATTRACTANT FOR INDIAN MEAL MOTH LARVE

FIELD OF THE INVENTION

The present invention relates to an attractant for Indian meal moth larvae.

BACKGROUND OF THE INVENTION

The Indian Meal Moth (*Plodia interpunctella*) is the most serious and wide spread moth pest of stored grains and grain products in the world. The pest has a huge economic impact on grain storage warehouses, as well as milling, packaging, and consumer-visited facilities (e.g. grocery stores, pet food markets, etc.).

In commercial facilities, the moths are controlled through fumigation with Methyl Bromide. However, this method of control is generally untenable at consumer visited facilities. Further, the future availability of Methyl Bromide is suspect and there is currently no substitute that has been approved for wide spread use. Additionally, the application of chemical pesticides directly to harvested food products is generally undesirable.

The need exists for means of controlling the Indian Meal Moth that does not require the application of chemical pesticides directly to harvested food products. The current invention provides a means of attracting adult and larvae meal moths to a variety of traps and thereby controlling the moth population.

SUMMARY OF THE INVENTION

The current invention is directed a composition comprising 2-pentyl furan and a carrier or carrier material so that the composition emits 2-pentyl furan vapors. The current invention is also directed to a method of attracting larvae of the *Polodia* species. The method includes treating an area or object with an effective amount of an attractant comprising 2-pentyl furan so that the larvae are drawn to the area or object.

BRIEF DESCRIPTION OF THE DRAWINGS

FIG. 2. Attraction of neonatal (A) and early penultimate instar (B) larvae to whole wheat. Samples of NASE placed at both ends of bioassay chamber bottom; wheat was suspended under the air inlet directly over one of the NASE samples. Error bars=±SD (total percentage of larvae found on NASE samples±SD)=total number of larvae on NASE samples/initial number of eggs or larvae added. * sample pair was significantly different at $P<0.05$ (t-test).

FIG. 3. Attraction of neonatal (A) and early penultimate instar (B) larvae to isolated whole wheat volatiles. Volatiles partitioning into an air stream (53 cc/min) passing through a 20 g column of wheat for 48 h were trapped on Super Q, eluted and aliquots placed on 3MM scintillation pads for bioassay. Error bars=±SD. (total percentage of larvae found on NASE samples±SD)=total number of larvae on NASE samples/initial number of eggs or larvae added. * sample pair was significantly different at $P<0.05$ (t-test).

FIG. 6. Attraction of neonatal (A) and early penultimate instar larvae (B) to different amounts of wheat germ oil transferred to 3MM scintillation pads that were placed on NASE samples for bioassay. Error bars=±SD. (total percentage of larvae found on NASE samples±SD)=total number of larvae on NASE samples/initial number of eggs or larvae added. * sample pair was significantly different at $P<0.05$ (t-test).

DETAILED DESCRIPTION OF PREFERRED EMBODIMENTS

Food attractants for stored product pests have generally not received as much attention as have sex attractants. In the cases where food attractants have been used, the attractant has generally comprised the food itself or a specific part of the food thought to desirable. The exact chemical source of the attractant has not been identified, and therefore the specific chemical attractant has not been concentrated or otherwise manipulated to increase the attractant's efficiency or effectiveness.

For moths, the use of an attractive food component has largely been viewed as a means to attract adult females where the food component acts as a lure for oviposition. Other uses for food attractants have been generally left unexplored. Only fragmentary information was previously available on whether the neonatal larvae subsequently follow the same odor to its source to initiate feeding.

However, the inventors determined that there is a volatile attractant originating in the wheat kernel that guides the larvae of the Indian meal moth (*Plodia interpunctella*) to the wheat kernel and subsequently to the wheat germ. The larvae feed exclusively on the wheat germ during their growth and development. One larva consumes multiple germs as it grows to maturity, relying upon the attractant to guide it from one germ to the next. Low levels of the attractant originate in the germ by the peroxidation of linoleic acid during the development of rancidity.

The inventors identified the chemical attractant that originates in the germ as 2-pentylfuran. As described infra, the inventors used mass spectroscopic analysis (among other things) to identify 2-pentylfuran as the key attractant component in the volatiles emanating from whole wheat, from wheat germ and from wheat germ oil. All larval stages of *Plodia* are attracted to picogram quantities of 2-pentyl furan when bioassayed.

The 2-pentyl furan attractant may be used with a carrier component. Multiple suitable carriers are well-known in the art and may be selected in accordance with a specific application and the needs of a particular user. The carrier component may be comprised of a variety solids or liquids consistent with the function of stabilizing the attractant and facilitating dispersion.

Similarly the attractant and carrier may be directly dispersed as a spray or simply exposed to the air in an open container. The attractant and carrier maybe dispersed in combination with various types of substrates and dispersal means including simple membranes, hollow fibers, microcapsules, cigarette filters, gels, polymers, septa, or the like. All of these substrates have been used to release insect attractants in general and should be considered within the scope of the invention. In the preferred embodiment, the carrier, carrier material, or substrates act as a slow release system for the 2-pentyl furan.

The attractant may be used in combination with any compatible insect trap known in the art. All mechanical, electrical, chemical, and biologically-based traps should be considered within the scope of the current invention.

Bioassay Chamber

Figure 1:
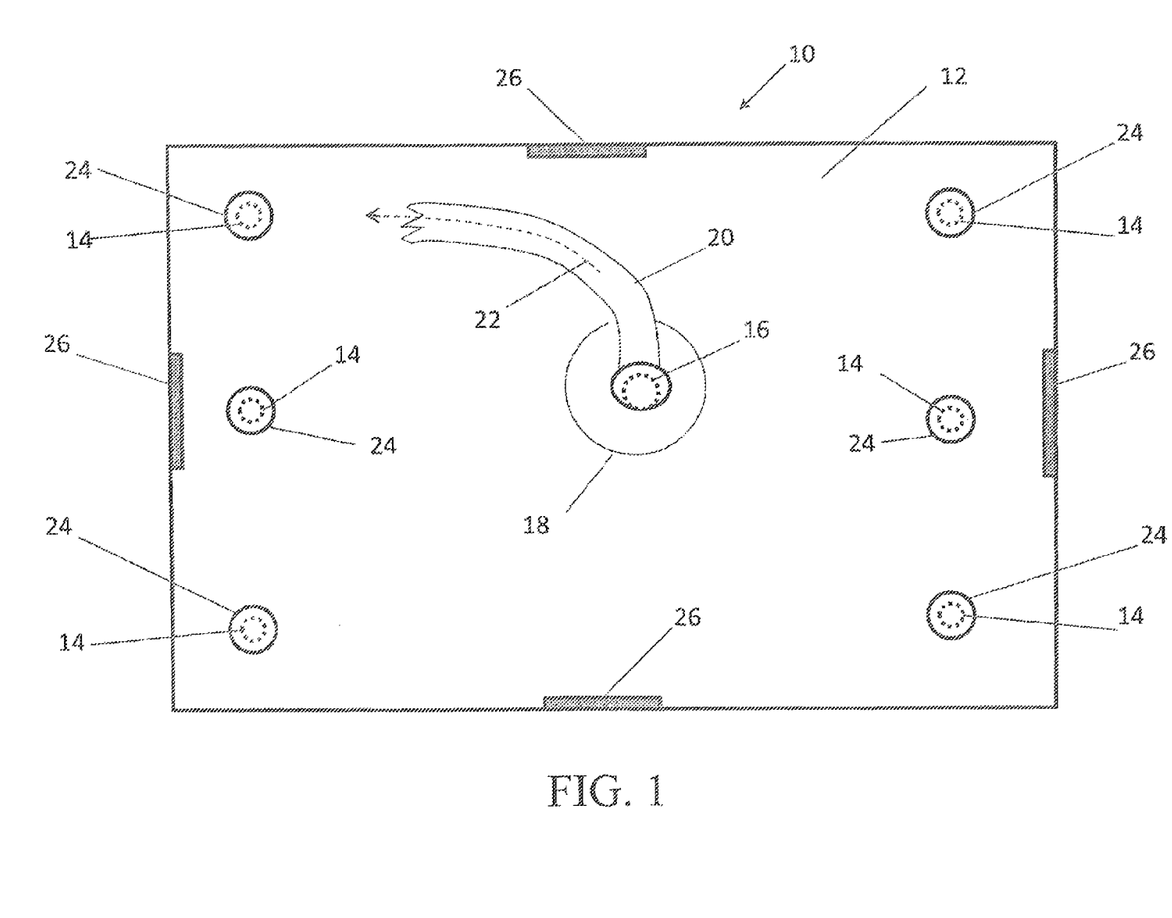
FIG. 1. Top (plan) view of the Bioassay Chamber.

To isolate the attractant, the inventors bioassayed multiple materials that potentially comprised effective attractants. To bioassay potential attractants, the inventors designed a custom bioassay chamber 10, as generally shown in FIG. 1. The bioassay chamber 10 was comprised of a Lincoln Wear-Ever (Fort Wayne, Ind.) baking pan (No. 9002) having the dimensions of 65 cm long, 45 cm wide and 2.5 cm high. A similarly sized Carb-x plastic top 12 (Rubbermaid Commercial Products Inc., Winchester, Va.) was modified for this application. (Note that FIG. 1 is a (top) plan view so that only the Carb-x plastic top 12 of the bioassay chamber is shown.)

As shown in FIG. 1, three evenly spaced 0.5 cm diameter holes 14 were drilled at each end of the top 12. The rows of three holes were ~8 cm from the outer edge at the ends and ~10 cm from the outer edge on the two sides, which spaced the three holes ~12.5 cm apart, center to center. A 3.0 cm diameter hole 16 was drilled in the center of the top 12 to accept a bulkhead fitting 18 (# 16422, United States Plastic Corp., Lima, Ohio) complete with a right angle connection and a serrated vacuum hose 20. During the bioassay process, air was drawn into the chamber 10 through the six air inlet holes 14 and removed from the chamber 10 through the fitting 18 and vacuum hose 20 in the direction of the arrow 22.

Before each bioassay, the chambers 10 were washed with a dilute solution of Micro-90 detergent (International Products Corp, Burlington, N.J.), rinsed 3 times with tap water, 1 time with distilled water, 1 time with MeOH and air dried. Test samples were placed in flat polypropylene weigh boats. An individual sample was positioned at each end of the chamber 10 under the middle air inlets.

The six air inlet holes 14 were fitted with syringe ports (Part # MTL230-6, Value Plastics, Inc., Fort Collins, Colo.) and six 10 cc syringes 24 filled with activated charcoal were affixed. Low-density foam weather strip (6.3 mm thick×12.7 mm wide, not shown in FIG. 1) was attached along the four edges of the top 12 to form an airtight seal when placed on the bottom pan and tightened together with four Sparco Binder Clips, # 87010 (2" wide, 1" capacity) 26. A vacuum means (not shown) was attached to the vacuum hose 20 was adjusted to give an exit flow of ~53 cc/min or one chamber volume (~2.4l) exchange every 45 min during the bioassay.

Experimental Insects

*Plodia* larvae used in this study were reared on a standardized *Plodia* diet (Silhacek and Miller, 1972) at 30° C., 70% r.h. and a 16L:8D photoperiod as described previously (Silhacek et al, 2003) using eggs collected over a 1 h interval during the 2 h period preceding the scotophase. Neonatal larvae used for bioassay were obtained by first incubating groups of eggs at rearing conditions for 54 h after oviposition. One-hundred 54 h eggs were then transferred to the 16 mm sample cup and placed on the release point at the center of the bioassay chamber that had equilibrated for 1 h in a dedicated incubator, maintained at 30° C., 70% r.h. and total darkness. The eggs hatched at ~64 h and the neonates had the choice of selecting the most attractive sample. After hatching, the neonates were given ~8 h to crawl to either of the test samples. The samples were then removed, mixed with *Plodia* diet and the larvae counted after two days of additional growth.

In addition to neonates, three other age groups of larvae were selected from the standardized cultures for bioassay to determine if they were attracted to the wheat grain and its components. These groups included newly molted penultimate instar (0.6±0.1 mg), newly molted last instar (3.2±0.2 mg) and mid-last instar (7.8±0.8 mg) (see Silhacek and Miller, 1972). In these assays, 10 larvae of the specified age, stage and weight range were transferred to the 16 mm sample cup at the beginning of the scotophase and immediately placed at the release point in the equilibrated bioassay chamber. The cover was secured to the chamber bottom and the larvae were given three hours to select the sample of choice and then the larvae on each sample were counted.

Attraction of Neonates and Earl Penultimates to Wheat Kernel Tissues

In the first set of tests, the relative attractiveness of the three major, commercially available kernel tissue fractions of wheat were assessed. The tissues were crude bran (Flint River Mills, Bainbridge, Ga.), Kretschmer's toasted wheat germ (Quaker Oats Co., Chicago, Ill.) and endosperm (organically grown, unbleached, unenriched all-purpose flour, Wards Super Market, Gainesville, Fla.). The relative attractiveness of these fractions was assessed in choice tests where two kernel tissuesfrations were placed at opposite ends of the bioassay chamber; neonatal or early penultimate instar larvae released between the two tissue samples had a choice of the two samples.

Isolation of Attractive Volatiles from Wheat Kernels and Their Constituents

The attractiveness of whole kernel wheat volatiles was examined by suspending a packet of whole wheat in the air stream entering the bioassay chamber over a sample of NASE. NASE is an olfactorily neutral food product consisting of wheat endosperm plus 10% sucrose (w/w; Dixie Crystals powdered sugar, Imperial Sugar Company, Sugar Land, Tex.) that provides some of the nutritive qualities sought by the larvae. Incorporating NASE into both the control and test samples provided stability in the bioassay by minimizing the wandering of attracted larvae from the test samples.

The basic procedure for isolating subsequent attractive volatile fractions from wheat kernels and its tissues was to pass an air stream through or over the potential volatile source (e.g. whole kernels or isolated kernel tissues) and trapping any entrained volatiles out of the air stream by passing it through Super Q. The volatiles were eluted from Super Q with $CH_2Cl_2$ and the eluate was transferred to 3 MM scintillation pads (23 mm filter paper discs, Whatman, Florham Park, N.J.) for bioassay. These bioassays were conducted by placing the test pad containing the volatiles on one of two NASE samples placed at opposite ends in the bioassay chamber and measuring the attraction of neonates or early penultimates to the two samples as previously described.

Specific Isolations of Wheat Kernel Volatiles

Volatiles from whole wheat were removed from an air stream passing through a column containing 20 g of kernels at a rate of 53 ml/min. The effluent was directed through a second column containing 50 mg of Super Q and vented to the atmosphere. After 24 h the Super Q column was removed from the collection system and washed with 0.4 ml of $CH_2Cl_2$ (J.T. Baker Chemical Co., Philipsburg, N.J.) to elute the volatiles. One portion of the eluate was prepared for bioassay of larval attraction and a second portion was prepared for mass spectrophotometric analyses.

Volatiles were isolated from 3 g of Kretschmer wheat germ using the same procedure as that described for whole wheat. The isolated fraction was bioassayed to verify the presence of the attractant. The remainder of the isolate was prepared for mass spectrophotometric analyses.

The attractive volatiles from wheat germ oil were isolated by transferring 385 mg of oil to a 3 MM scintillation pad and then placing the pad in a flowing (53 ml/min) air stream for 24 h. The volatiles were collected on Super Q as previously described. A portion of the volatile fraction that were recovered from the Super Q was bioassayed for attractancy and the remainder was prepared for mass spectrophotometric analyses.

Bioassay of Purified Attractant

After the wheat germ attractant had been identified, the attractant activity in various extracts and preparations has been monitored by either the neonate or early penultimate bioassays. The penultimate bioassay is more convenient and rapid to use for routine analyses. Samples are usually transferred to 3 MM scintillation pads for bioassay.

Mass Spectral Analyses

Volatiles eluted from Super Q filters were analyzed both by chemical ionization (CI) and electron impact (EI) mass spectroscopy using a Finnigan-Matt ITS 40® ion trap mass spectrometer (MS). The MS was interfaced to a Varian Star 3400® gas chromatograph (GC) equipped with a cool-on-column injector. The anaytical column, a 30 m×0.25 mm (id) uncoated, deactivated fused silica retention gap and a 10 cm×0.5 mm (id) length of uncoated, deactivated fused silica in the injector.

Conditions of chromatography were: initial injector temperature=40° for 30 sec; injector temperature increased at 170°/min to 270°; initial column temperature=40° for 5 min; column temperature increased at 5°/min to 210°; He carrier gas linear flow velocity=24 cm/sec; GC-MS transfer line temperature=230°. When operated in the chemical ionization (CI) mode isobutene served as reagent gas. For all analyses the mass acquisition range was from 30-350 amu; scan rate=1 sec). Tentative structural assignments of natural products were obtained from comparison of spectra with those available in the NIST mass spectral library data base and from a data base generated by us. Further structural proof was obtained by comparing GC retention times and fragmentation patterns (both EI and CI) of authentic synthetic standards with those of compounds in the natural product samples.

Analysis of Bioassay Results

All means reported were obtained by averaging three distinct observations. Sample means were tested using a two-sample t-test assuming unequal variances (Microsoft Excel 2003 data analysis). P value reported is (T<=t) two tail. Variances were likewise tested using the same software to determine F.

Attraction of Neonates to Whole Wheat Kernels

Figure 2:
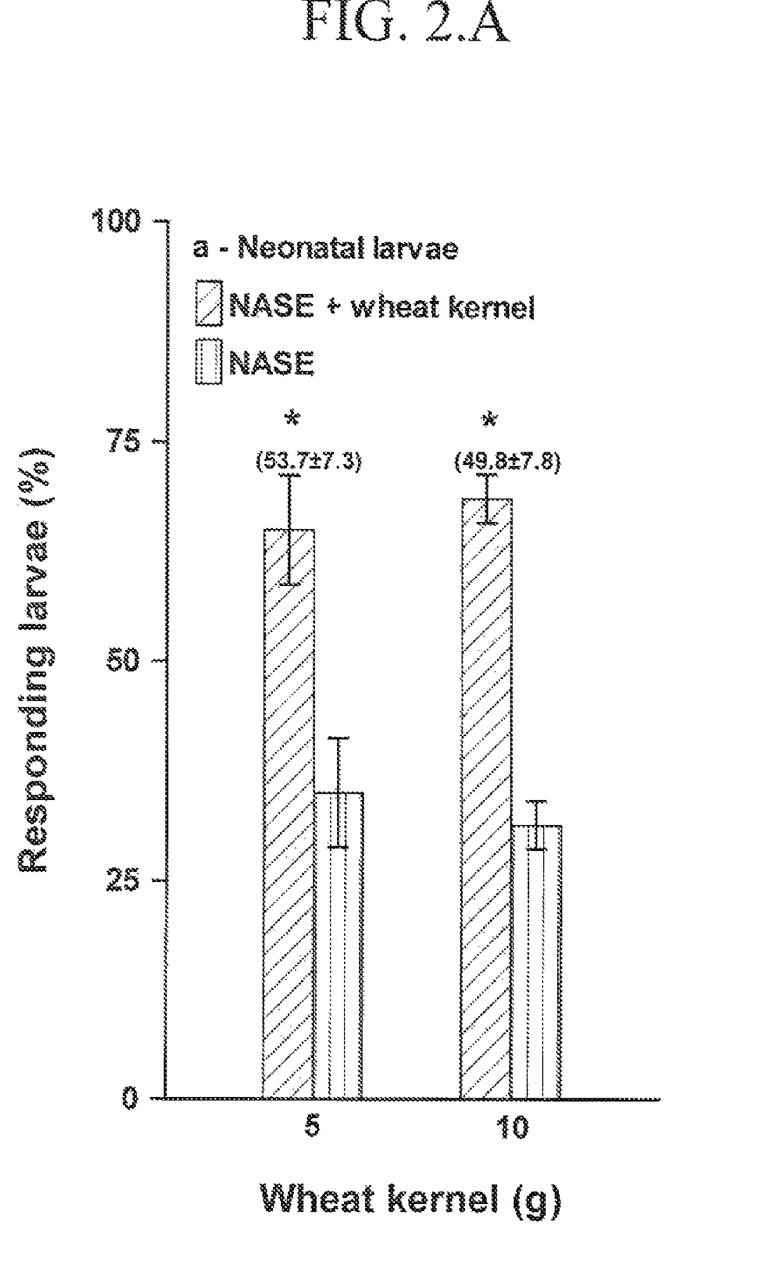

The first experiment was directed at determining if whole kernel soft wheat (Arrowhead Mills, Inc., Melville, N.Y.) was attractive to *Plodia* neonates. To test this, a 5 g packet of whole wheat kernels was suspended over a sample of NASE and bioassayed against a second sample of NASE. About 70% of the responding neonatal larvae in the bioassay chamber moved to the sample of NASE under the packet of wheat kernels (FIG. 2(A). Increasing the kernel amount to 10 g did not increase the number of neonates attracted, indicating that both kernel samples were providing maximum attraction. Over 80% of the older 0.6 mg larvae were attracted to similar sized packets of whole wheat kernels (FIG. 2(B). As with the neonates, the 0.6 mg larvae did not show an increase in attraction when the amount of kernels was doubled. These results indicated that whole wheat was the source of a chemical that was attractive to *Plodia* larvae which guided them to the intact kernels of whole wheat.

Figure 3:
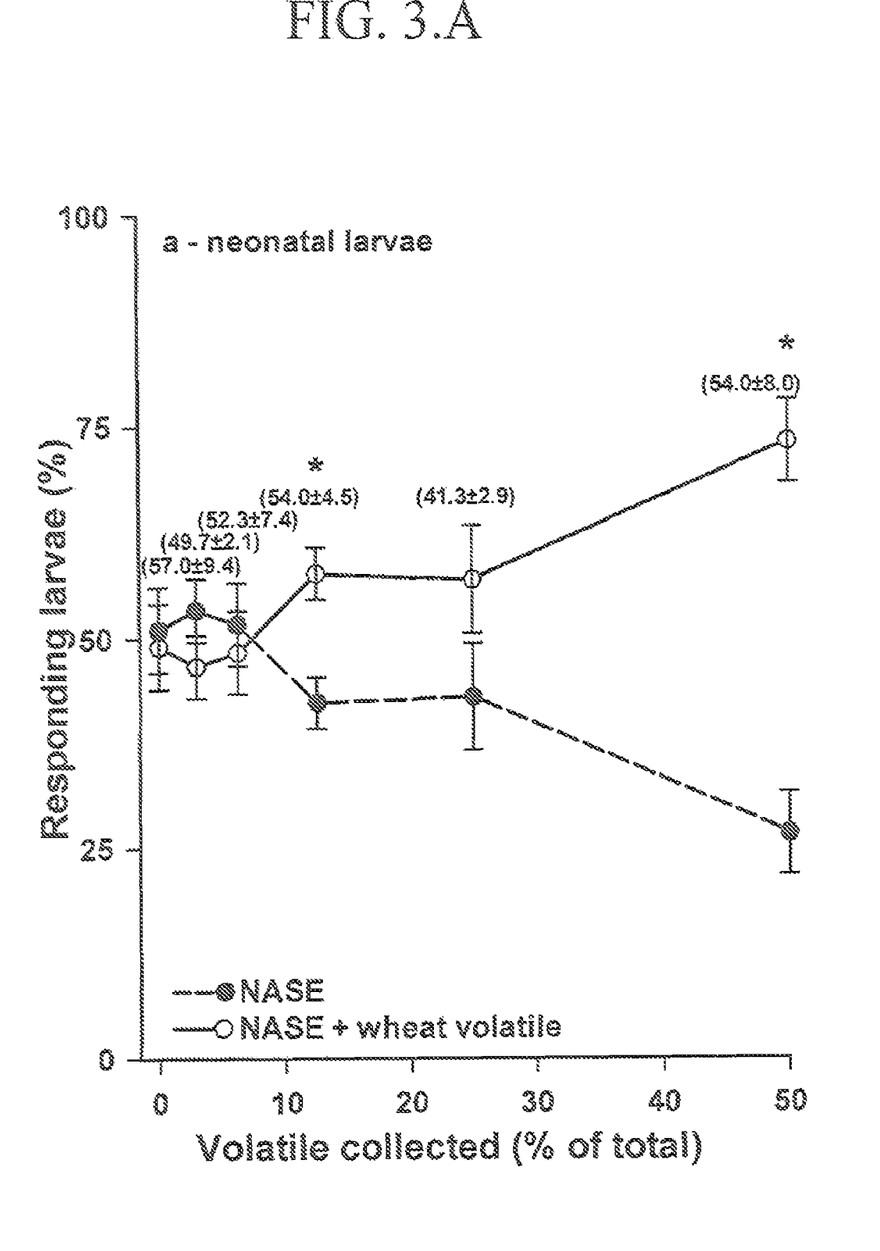

The observation that a volatile attractant was emanating from whole wheat was reinforced by the demonstration that an airstream, passing through a column of 20 g of whole wheat kernels for 48 h, transferred an attractive mixture of whole wheat volatiles to a column of Super Q. Subsequently, the whole wheat volatiles were eluted from Super Q and bioassayed to determine their attractiveness. Both, neonates and 0.6 mg larvae, were strongly attracted to samples of NASE on which 3MM scintillation pads containing the whole wheat volatiles from Super Q were placed. The results of these tests confirmed that *Plodia* larvae were attracted to one or more volatile chemicals originating in whole wheat FIG. 3(A) and (B).

Attraction of Neonates to the Major Tissues in the Wheat Kernel

Figure 4:
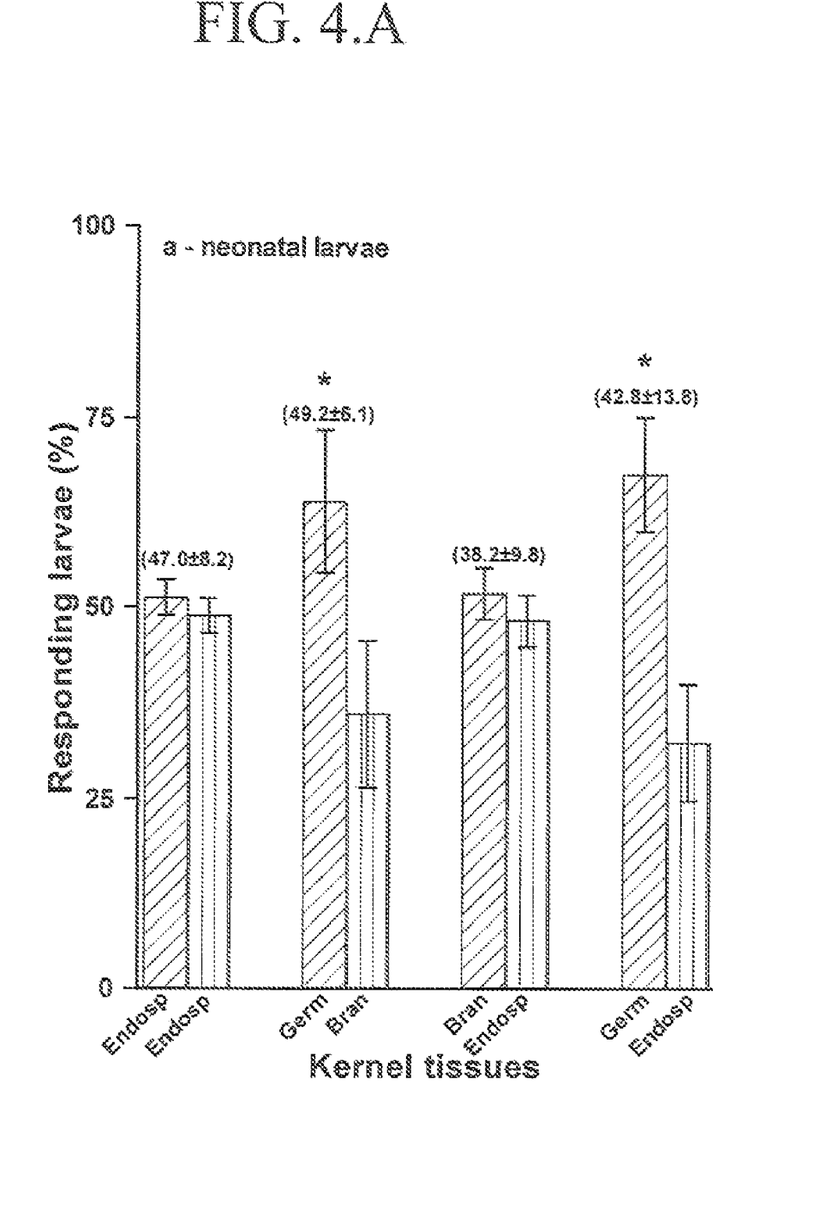
FIG. 4 and FIG. 5. Attraction of larvae at different stages of development to the three major tissue fractions (bran, germ, and endosperm) commercially prepared, from whole wheat Error bars=±SD. (total percentage of larvae found on NASE samples±SD)=total number of larvae on NASE samples/initial number of eggs or larvae added. * sample pair was significantly different at $P<0.05$ (t-test).

Identifying which of the kernel tissue(s) was the source of the attractant(s) was accomplished using a paired attraction bioassay method. In these assays, two different tissue samples were placed at opposite ends of the bioassay chamber and the larvae, placed between the two samples, had to choose the most attractive tissue. The results of these paired attraction assays (see FIG. 4) indicated that of the three wheat kernel tissues, only germ consistently attracted the most larvae.

As larvae grow to maturity, they continue to feed exclusively on the germ (Silhacek and Murphy, unpublished observation). Thus, the older larvae must find the germs of successive kernels by orienting to some unique characteristic of the germ. The inventors examined early penultimate instar larvae and found that they too were attracted to the wheat germ volatiles isolated on Super Q. This indicated that the older larvae were probably orienting to the same attractant as the neonates when searching for a suitable food source.

Attractancy of Wheat Germ Oil

Figure 5:
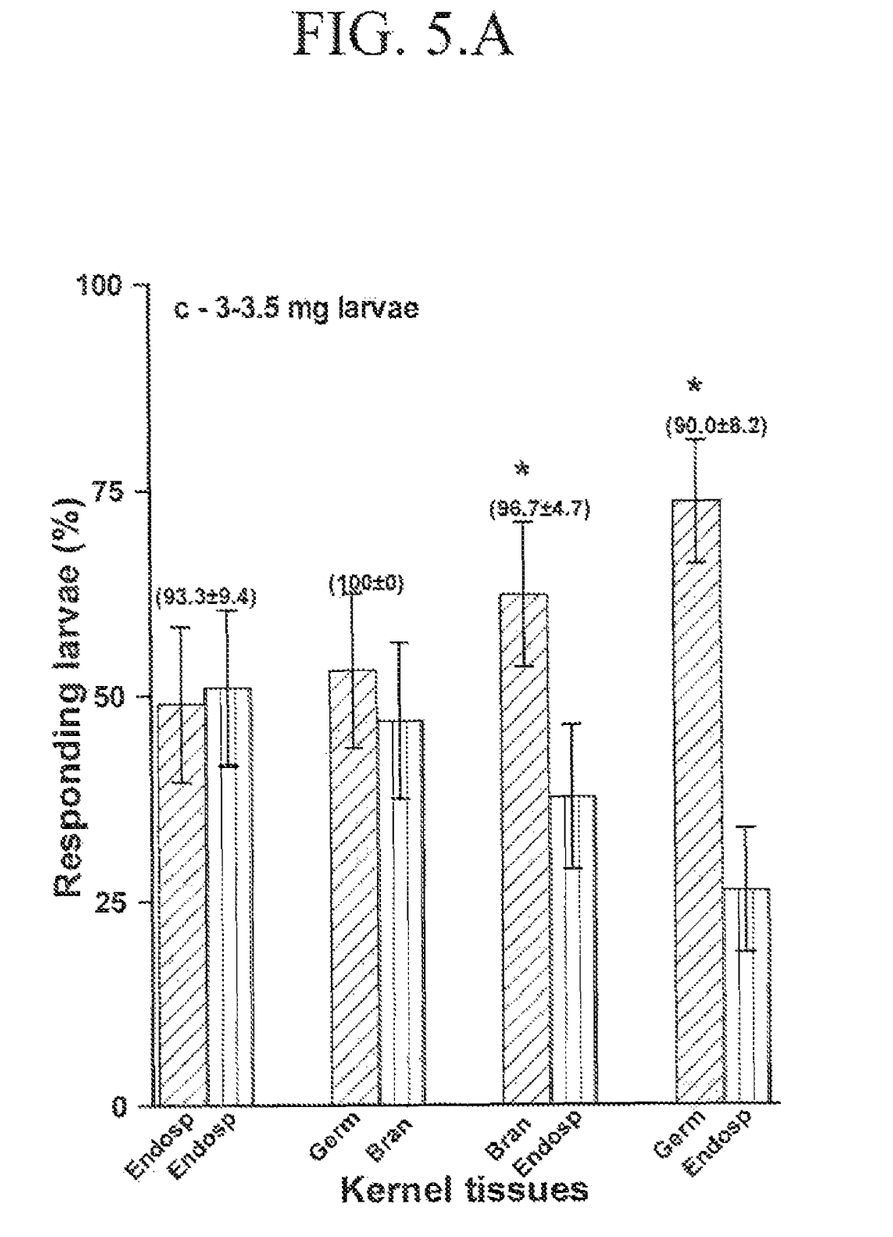
Figure 6:
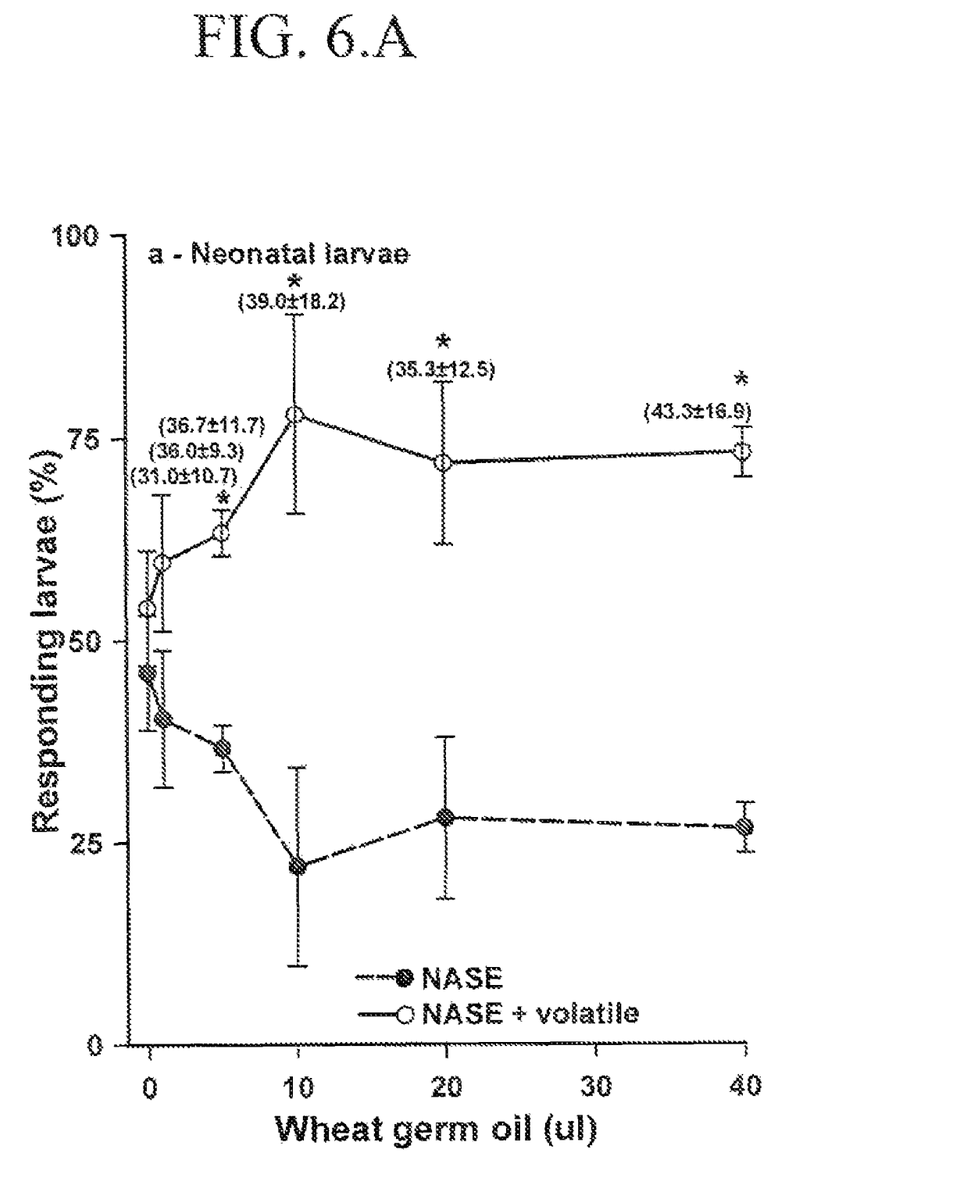

The volatile character of the that it might be found in the oil expressed from wheat germ. Wheat germ oil (cold-processed wheat germ oil, Standard Process Inc., Palmyra, Wis.), which constitutes ~12% of the germ (Mecham, 1978), mainly consists of 13 fatty acids with palmitic (17.7%), oleic (10.9%), linoleic (58.2%)and α-linolenic (93%) constituting over 96% of the total fatty acids (Sjovall, et al., 2000). When different quantities; ranging from 40 µl down to 1 µl, of wheat germ oil were bioassayed, 0.6 mg larvae were strongly attracted to all levels of the oil (FIG. 5*b*). The inventors subsequently found that this strong attraction of 0.6 mg larvae was abruptly lost at wheat germ oil levels below 0.1 µl. Bioassays of wheat germ oil using neonates showed a similar response range (FIG. 6).

Chemical Identity of the *Plodia* Attractant

Figure 7:
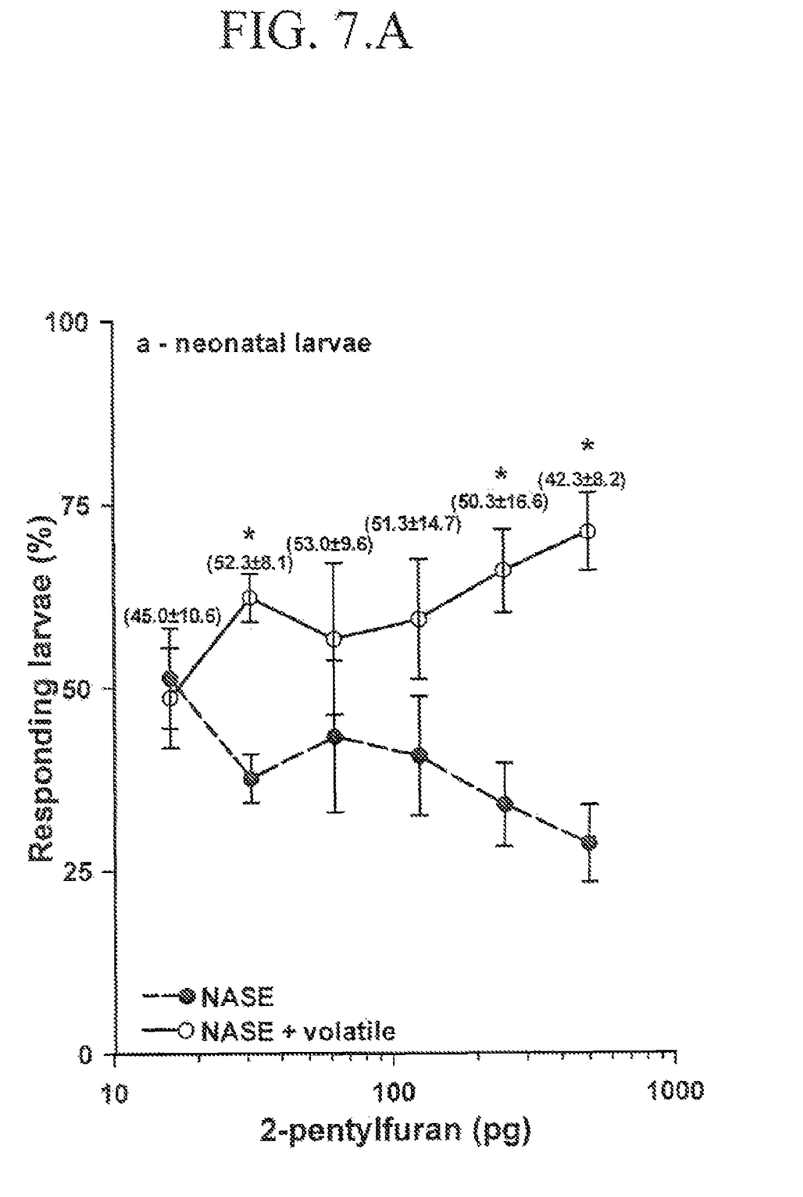
FIG. 7 and FIG. 8. Attraction of larvae at different stages of development to different amounts of 2-pentylfuran transferred to 3MM scintillation pads that were placed on a NASE samples for bioassay. Error bars=±SD. (total percentage of larvae found on NASE samples±SD)=total number of larvae on NASE samples/initial number of eggs or larvae added. * sample pair were significantly different at $P<0.05$ (t-test).
Figure 8:
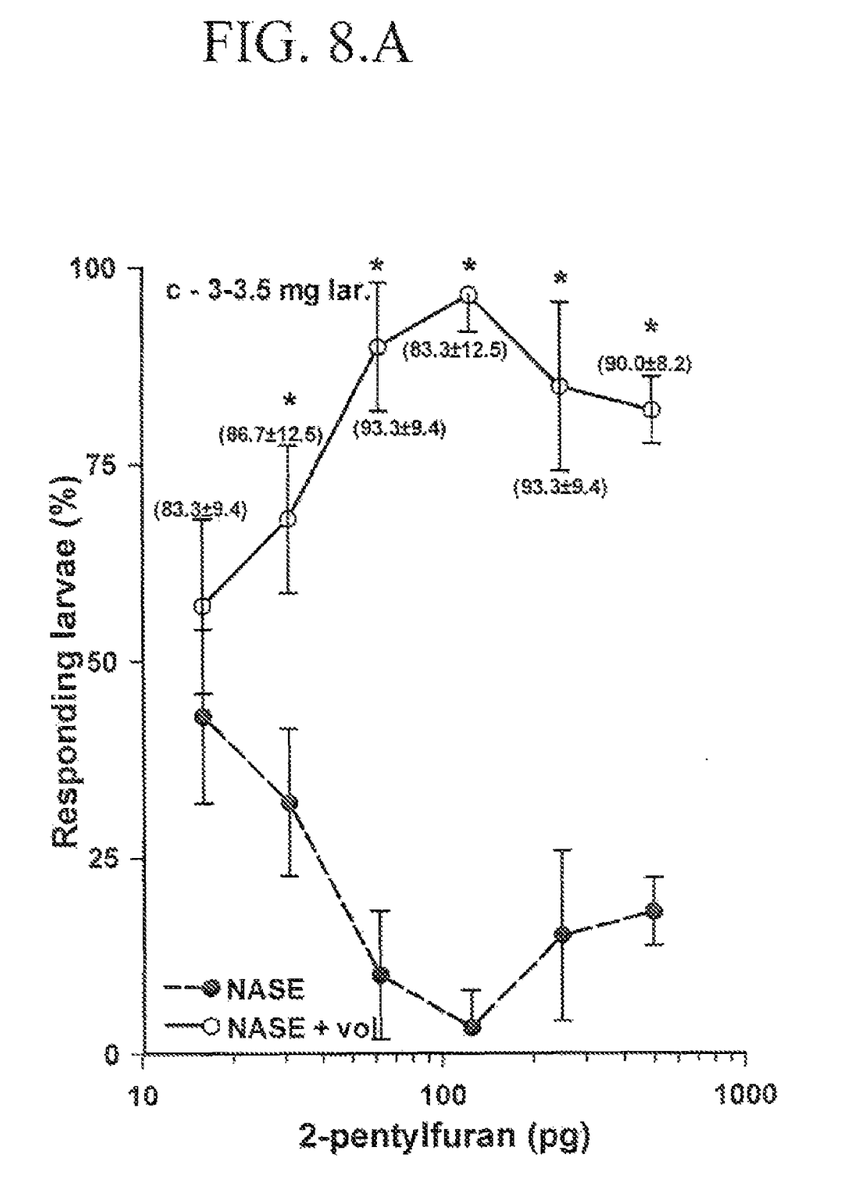

The germ is particularrly susceptible to the development of rancidity because of its high lipase and lipoxygenase activities and its high content of unsaturated fatty acids (Sjovall, et al., 2000). The oxidation of unsaturated fatty acids in cereal grains has been shown to produce volatile compounds that contribute to the odors that are formed during the development of rancidity (Hein, 2002). Sjovall, et al. (2000) identified 35 volatile compounds in the headspace above stored wheat germ as part of their studies on rancidity. Two reactions that contribute to the rancidity of wheat germ are the oxidation of linoleic and linolenic acids which results in the formation of two very volatile products, 2-pentyl-furan and hexanal, respectively (Hein, et al., 2002). Mass spectroscopic analyses confirmed that both, hexanal and 2-pentyl furan, were present in the volatiles of the wheat germ used in the attraction studies reported here. Both compounds appeared to satisfy the volatility and dissipation criteria postulated for an effective *Plodia* food attractant in stored grain. Hexanal and 2-pentyl furan were obtained from Aldrich Chemical Company (Milwaukee, Wis.), serially diluted and bioassayed for attractancy with neonates over the range of 16 pg to 500 pg. Hexanal was not attractive to *Plodia* neonates at any of the concentrations tested. In contrast, 2-pentylfuran was attractive at all levels tested between 32 and 500 pg (FIGS. 7 and 8). There was very little graded attractant response, but rather an abrupt transition from no attractancy to attractancy with increasing concentrations of 2-pentyl furan. A similar abrupt transition in attractancy was observed when wheat germ oil was bioassayed (FIG. 6).

An even clearer picture was observed when older larvae were bioassayed with 2-pentyl furan. Moderate but not significant attraction was first observed with 31 pg of 2-pentyl furan on the 3MM scintillation pad used for bioassay at the three older age groups (FIGS. 7 and 8). Peak attraction was observed over the range of 62.5-125 pg. Strong attraction was also observed over the range of 250-500 pg, but the capture of larvae in the non-attractive NASE sample may indicate some confusion at the higher levels of 2-pentyl furan. Larval attraction to 2-pentyl furan was strong through the middle (7.0-8.5 mg) of the final larval, instar. Disturbing larvae weighing more than 9 mg usually triggered spinning behavior and early pupation which diminished their response to the food attractant.

The detection of such low levels of 2-pentyl furan by the larva would indicate that the larval receptor has a strong affinity for the attractant (low Kd). This characteristic of the receptor would account for the very sharp response threshold to low levels of the attractant. In the stored grain environment a high-affinity receptor would function most effectively with an attractant that had high volatility, a short half-life and a low-level release rate which would facilitate the attractant's rapid dispersal and dissipation. All of these attractant characteristics are manifested by 2-pentylfuran.

Verifying the Natural Occurrence of 2-Pentyl Furan

The inventors observed earlier that whole wheat kernels produced a volatile chemical that attracted *Plodia* larvae to the kernel that led to the consumption of the germ. If 2-pentyl furan is the attractant the larvae are responding to, then 2-pentyl furan should be present in the volatiles given off by whole wheat kernels. This was tested by passing an air stream through a column containing 20 g of undamaged whole kernel wheat for 24 h and collecting the volatiles in the air stream on Super Q as it exited the column of wheat. The volatiles trapped on Super Q were eluted with $CH_3Cl$ and analyzed by mass spectrometry. The analysis indicated that 2-pentyl furan was present in the volatiles collected from whole wheat kernels.

The larva's ultimate objective is to reach the germ so that it can ingest the germ nutrients. Since the germ is attractive to the larvae, then it follows that the germ must be giving off 2-pentyl furan. The inventors tested this conjecture by passing air through a column of wheat germ and collecting the volatiles on Super Q. The volatiles were removed from the Super Q by washing with $CH_2Cl_2$ and analyzing the volatiles by mass spectrometry. The analyses revealed that 2-pentyl furan was present in the volatiles given off by wheat germ.

When wheat germ oil was analyzed by mass spectrometry there was no evidence that 2-pentyl furan was in the oil. However, the inventors demonstrated that the oil was attractive to *Plodia* larvae, which created a dilemma that had to be resolved. One possibility was that the 2-pentyl furan concentration was too low to detect. In a subsequent test, 385 mg of wheat germ oil was transferred to 3MM scintillation pads, placed in an air stream for 24 h and the volatiles partitioning into the air stream were collected on a column of Super Q. Analyses of the volatiles trapped on Super Q revealed that 2-pentyl furan could be seen in this more concentrated sample of wheat germ oil volatiles. This observation supported the bioassay data (FIG. 6 which showed that, the attractant was being released from wheat germ, oil.

CONCLUSIONS

Neonatal and older larvae of *Plodia interpunctella* are attracted to whole wheat kernels by a volatile attractant originating in the germ. The attractant guides the larvae to the germ for its nutrition and growth. The attractant, 2-pentyl furan, is an oxidation product of linoleic acid that is normally formed at low levels during the storage of whole grain. The lability and volatility of 2-pentyl furan along with its slow rate of formation are properties ideally suited for an insect attractant that functions in a stored grain environment. The very low levels of 2-pentyl furan formed in the germ of wheat guides all larval stages of *Plodia interpunctella* to the germ in the wheat kernel.

For the foregoing reasons, it is clear that 2-pental furan provides an innovative insect attractant that may be used in multiple forms and applications. The invention may be modified in multiple ways and applied in various technological applications. The current invention may be modified and customized as required by a specific operation or application to achieve the desired result. Such variations are not to be regarded as a departure from the spirit and scope of the invention, and all such modifications as would be obvious to one skilled in the art are intended to be included within the scope of the following claims.

What is claimed is:

1. A synthetic insect attractant composition comprising 2-pentyl furan and a carrier or carrier material so that the composition emits 2-pentyl furan vapors.

2. The composition of claim 1 wherein the insect attractant attracts *Plodia* species.

3. The composition of claim 2 wherein the insect attractant attracts *Plodia* larvae.

4. The composition of claim 1 wherein the carrier or carrier material acts as a slow release system.

5. A method of attracting larvae of the *Plodia* species, the method comprising treating an area or object with an effective amount of an attractant comprising the composition of claim 1 so that the larvae are drawn to the area or object.

* * * * *